United States Patent [19]  [11] 4,021,565
Berger  [45] May 3, 1977

[54] PROCESS FOR THE ALLEVIATION OF DEPRESSION BY ADMINISTRATION OF NON-ADDICTING MEPERIDINE ANALOGUES

[76] Inventor: Frank M. Berger, 190 E. 72nd St., New York, N.Y. 10021

[22] Filed: Jan. 29, 1976

[21] Appl. No.: 653,804

Related U.S. Application Data

[63] Continuation of Ser. No. 566,587, April 8, 1975, abandoned.

[52] U.S. Cl. ............................................... 424/267
[51] Int. Cl.² ..................................... A61K 31/445
[58] Field of Search ............... 424/267; 260/293.81

[56] References Cited
OTHER PUBLICATIONS
Chem. Abst., vol. 62 – 945g (1965).
Chem. Abst., vol. 75 – 74399g (1971).
Chem. Abst., vol. 72 – 136331c (1970).

Primary Examiner—Stanley J. Friedman

[57] ABSTRACT

A process is provided for the alleviation of depression by administration of merperidine analogues corresponding to the formula:

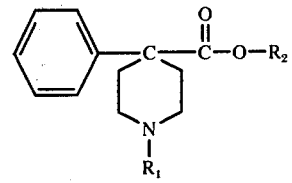

in which $R_1$ and $R_2$ are each lower alkyl or allyl.

10 Claims, No Drawings

PROCESS FOR THE ALLEVIATION OF DEPRESSION BY ADMINISTRATION OF NON-ADDICTING MEPERIDINE ANALOGUES

This is a continuation of application Ser. No. 566,587 filed Apr. 8, 1975 now abandoned.

Depression is a very common condition characterized by symptoms such as depressed mood, loss of interest, loss of pleasure, loss of appetite and sexual desire, lack of energy, sleeplessness, and suicidal tendencies. Mild forms of the condition often occur in response to a personal loss, such as the death of a loved one. The condition is often transitory, but while it exists it can nonetheless be a severe problem, particularly in the case of a suicidal tendency, which may be consumated before the condition works itself out. In the more serious forms of the condition, sometimes also referred to as endogenous depression, a primary physical disturbance of the amine metabolism of the brain is suspected, as at least a contributory if not a casual factor.

It is sometimes very important to be able to alleviate the condition promptly. In the case of a suicidal tendency, for example, tragic consequences may ensue if the condition cannot somehow be rapidly counteracted or controlled. However, up to the present time no wholly effective or even satisfactory treatment of serious depressive states has been available.

The most effective treatment in widespread use is application of electric currents to the head to produce an electroconvulsive seizure. A number of electric shock treatments are usually required for a sufficient effect. Electric shock treatments can, however, have quite unfortunate consequences and side effects, as a result of which many physicians are reluctant to administer them. They may cause fractures and other physical injuries to the patient. Not infrequently, they result in partial loss of memory, or varying degrees of mental deterioration, which may last for a long time, if indeed they are not permanent.

Chemical treatment has been less effective, however, as a result of which electric shock treatments must be resorted to in serious cases, where prompt alleviation is prerequisite.

The so-called tricyclic antidepressant agents, introduced in the late 1950's, are effective only in a proportion of patients, and are quite slow to show a noticeable effect, frequently evidencing alleviation of the condition only after the patient has been taking them for two or three weeks. This is too long a time to wait for an alleviation in the case of a patient having a suicidal tendency, for example.

The monoamine oxidase class of antidepressant agents is used only in patients which are refractory to other treatments, because of their toxicity and unpredictable effectiveness and side effects.

Meperidine hydrochloride is an analgesic widely used for the relief of severe pain, and has the structure:

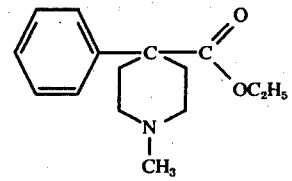

It has been sold in many countries under the trade names Demerol, Dolantin, Pethidine and others. It is among the classes of compounds disclosed and claimed in U.S. Pat. No. 2,167,351 issued to Eisleb on July 25, 1939; see column 1, page 2, lines 18 to 22, and claim 8. However, meperidine hydrochloride may be rapid and powerful in its addicting tendency.

In accordance with the invention, it has been determined that meperidine hydrochloride and certain meperidine analogues, closely similar to merperidine in structure, and even homologous thereto, having a lower alkyl or allyl substituent attached both to the nitrogen of the piperidine nucleus and to the carboxylic group attached to the piperidine nucleus as a side chain, are quite effective in alleviating depression. Meperidine hydrochloride is quite effective in alleviating depression, and the effect of the chemical is usually noticeable within a few hours. However, it cannot of course be employed in the treatment of depression, because of its narcotic and habit-forming or addictive qualities. The difficulty is that depression, particularly in its more serious forms, is a recurrent condition, that may require treatment for protracted periods of time, and may recur even after it has apparently been completely cured. For these reasons, it is neither appropriate nor advisable to treat depressive conditions with any drugs possessing a marked addictive or habit-forming potential. Surprisingly, however, the meperidine analogues are substantially nonaddictive and non-habit-forming in the amounts effective to alleviate depression. The amounts required for addiction are well in excess of these amounts. As a result, these compounds of the invention can safely be used in treatment of depression without addiction consequences.

The nonaddictive compounds of the invention are believed to be new as pharmaceuticals, and are defined by the formula:

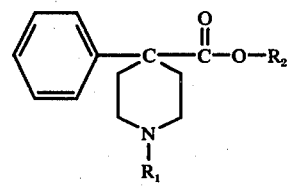

In the above formula, $R_1$ is lower alkyl having from one to four carbon atoms or alkyl and $R_2$ is alkyl having from one to two carbon atoms; but if $R_1$ is methyl or ethyl, $R_2$ is other than ethyl. Accordingly, these compounds differ from meperidine in that $R_1$ can be alkyl higher than methyl, or alkyl, and $R_2$ can be methyl.

The phenyl ring attached as a side chain to the 4-carbon atom of the piperidine ring and also bearing the carboxylic acid ester group can have inert substituents without material effect on antidepressive activity. Such inert substituents include, for example, halogen, such as fluorine, chlorine and bromine; lower alkyl, such as methyl, ethyl and propyl; and haloalkyl, such as trifluoromethyl.

These compounds are known compounds, and can be synthesized by known procedures. There can be used, for instance, the general procedure used for the preparation of meperidine. This procedure, as described by Eisleb, Ber. 74 1433 (1941), involves the condensation of the corresponding phenyl acetonitrile with the corresponding bis-β-chloroethylalkyl amine to give 4-phenyl-1-alkyl-piperidine-4-nitrile, which is then converted into the corresponding ethyl ester. The procedure can be outlined as follows:

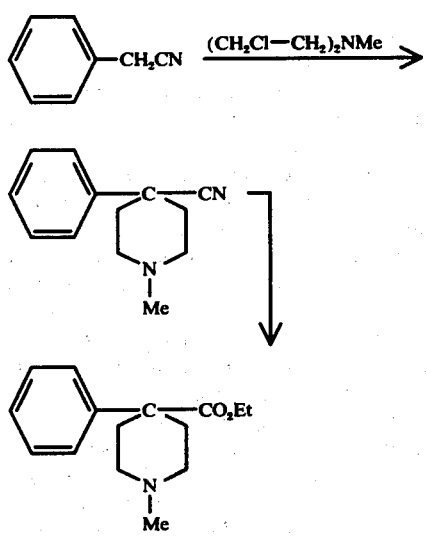

Another synthesis has been proposed by Walton and Green, *Journal of the Chemical Society* 1945 315, which avoids the use of the vesicant bis-β-chloroethylalkyl amine, employing 4-cyano-4-phenylpentamethylene oxide, which is converted into α,α-bis-β'-bromoethyl-phenyl acetic acid, and this is then treated as the ethyl ester with the corresponding alkyl amine. See also Bergel, Morrison and Rinderknecht *Journal of the Chemical Society*, 1944 267. Using this procedure, Walton and Green were able to prepare ethyl-4-phenyl-1-ethyl-piperidine-4-carboxylate; ethyl-4-phenyl-1-n-propyl-piperidine-4-carboxylate; and ethyl-4-phenyl-1-n-butyl-piperidine-4-carboxylate.

Another procedure is described in a later paper by Thorpe and Walton, *Journal of the Chemical Society* 1947 559, by alkylation of norpethidine:

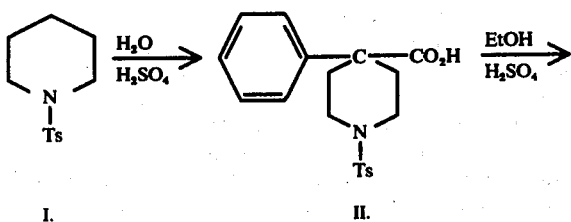

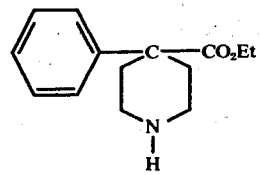

III.

Using this procedure these workers were able to prepare the N-ethyl, N-n-propyl, N-isopropyl, N-n-butyl, N-secondary-butyl, N-n-amyl, N-1'-methylbutyl and N-allyl derivatives of meperidine.

Thorpe and Walton studied the toxicity and analgesic activity of these compounds as compared to pethidine (meperidine) and found them slightly more effective as analgesics then pethidine, but not sufficiently different from or more potent than pethidine to prove of greater value. The toxicity increased slightly with the length of the alkyl chain, but the toxicity data reported shows no serious toxicity for any of them.

The compounds can be prepared and used in the form of the free amine or as a pharmaceutically acceptable salt including acid addition salts.

The acid addition salts include the pharmaceutically acceptable non-toxic addition salts with inorganic acids, for example, hydrochloric, hydrobromic, nitric, sulphuric or phosphoric acids, and with organic acids, for example acetic, glycollic, maleic, tartaric, citric, acetyloxy-benzoic, nicotinic or isonicotinic acids, methane sulphonic, ethane sulphonic, 2-hydroxyethane sulphonic, p-toluene sulphonic or naphthalene-2-sulphonic acids.

The following Examples illustrate preferred embodiments of the invention:

EXAMPLES 1 to 4

The antidepressant activity of the compounds in accordance with the invention has been evaluated in the Dopa response potentiation test described by G. M. Everett in "Antidepressant Drugs", Excerpta Medica Foundation, Amsterdam and New York 1967, pp. 164–167. This test is widely used in screening compounds for antidepressant activity, and is generally recognized in the field of psychopharmacology as being one of the best available tests for this purpose.

The test is based on the observation that the behavioral response to Dopa (3,4-dihydroxyphenyl)-L-alanine), the precursor of the neurotransmitters dopamine and norepinephrine, is modified by antidepressants in the presence of monoamineoxidase inhibition. Under these conditions, antidepressants given prior to Dopa potentiate the behavioral response usually seen after administration of Dopa.

The following Examples illustrate the activity of the compounds:

In this test, mice are pretreated with parglyine (1% solution parglyine HCl, 40 mg/kg) orally, 16 hours prior to the test. The test drug is injected one hour prior to the intraperitoneal administration of L-Dopa (1% solution). The intensity of the L-Dopa syndrome is recorded on a scale from 1 to 3, maximal response being 3+:

1+ Piloerection, slight salivation, slight increased motor activity.

2+ Piloerection, salivation, marked increased activity & irritability.

3+ Piloerection, profuse salivation, marked increased irritability & reactivity, jumping, squeaking and aggressive fighting.

Table I lists the compounds in accordance with the invention that have been tested in the Dopa response potentiation test, and compares them with similar compounds in the meperidine series. The smallest dose of the compounds producing maximum response in the test is also given in the Table. For comparison, the results obtained with the standard antidepressant drug Imipramine are also given, as are the results obtained in control animals that have not been treated with any drug.

TABLE I

| Compound | $R_1$ | $R_2$ | Dose mg/kg | Rating Dopa syndrome |
|---|---|---|---|---|
| Control | — | — | — | 1+ |
| Imipramine | — | — | 10 | 3+ |
| Meperidine | methyl | ethyl | 10 | 3+ |
| Normeperidine | H | ethyl | 25 | 2+ |
| Example 1 | n-propyl | ethyl | 25 | 2+ |
| Example 2 | allyl | ethyl | 25 | 3+ |
| Example 3 | n-butyl | ethyl | 25 | 3+ |
| Example 4 | methyl | methyl | 25 | 3+ |

The test results given in Table I show that maximum response in the Dopa test can be obtained with imipramine, meperidine, and the compounds of Examples 2, 3, and 4. The results indicate that these compounds possess strong antidepressant properties. Normeperidine and the compound of Example 1 gave a weaker response in the test, and are likely to have a weaker antidepressant action, but they are nonetheless sufficiently effective to be of interest.

The addictive tendency of the compounds of the invention was also evaluated, as compared to meperidine and normeperidine, using the morphine withdrawal test described by Leong Way, Loh and Hsiung in the *Journal of Pharmacology and Experimental Therapeutics* 167 1-8 (1969).

This test involves priming mice with morphine injections prior to the implantation of a 75 mg. morphine pellet subcutaneously. Removal of the pellet after 3 days results in a time-dependent withdrawal syndrome, which is characterized strikingly by a non-controllable urge to jump. This response can be selectively suppressed by morphine, and other agents possessing similar addictive properties, such as meperidine. Thus, the jumping response can be used as an index for estimating the degree of physical dependence or addiction. With abrupt withdrawal, the incidence of withdrawal jumping is time-dependent, the response being maximal 6 to 8 hours after removal of the morphine pellet. Abrupt abstinence is quantified by placing the animals on a circular platform, 35 centimeters in diameter and 70 centimeters high, and recording the percentage of animals that less off within 15 minutes.

In the test, all compounds were given at a dose of 50 mg/kg, and the percent antagonism of withdrawal jumping determined. Complete or 100 percent antagonism means that the compound possessing this effect could completely replace morphine, and for this reason is as habit-forming or addictive as morphine. The lower the antagonism percent figure, the lower the addictive tendency of the compound.

Table II gives the results of the test for compounds in accordance with the invention and near homologues thereof, including meperidone and normeperidine.

TABLE II

| Compound | $R_1$ | $R_2$ | Percent antagonism of withdrawal jumping |
|---|---|---|---|
| meperidine | methyl | ethyl | 100 |
| normeperidine | H | ethyl | 75 |
| Example 1 | n-propyl | ethyl | 25 |
| Example 2 | allyl | ethyl | 25 |
| Example 3 | n-butyl | ethyl | 25 |
| Example 4 | methyl | methyl | 50 |
| A | methyl | n-propyl | 75 |
| B | methyl | n-butyl | 100 |
| C | ethyl | n-propyl | 75 |
| D | ethyl | iso-propyl | 100 |
| E | ethyl | ethyl | 75 |
| F | n-pentyl | ethyl | 75 |
| G | benzyl | ethyl | 75 |

It is apparent from the results that the compounds in accordance with the invention are only one-third to one-fourth as addictive or habit forming as meperidine, and considerably superior to its near homologue, normeperidine. It is thus shown that $R_1$ should have three or four carbon atoms, to avoid the addictive tendency of meperidine and normeperidine, if $R_2$ is ethyl. Surprisingly, if $R_1$ and $R_2$ are each methyl, the compound is relatively nonaddictive, even though the compound is addictive when $R_1$ and $R_2$ are each ethyl (E). The results show addictive tendency is not correlated with antidepressant effectiveness, and that it is possible for a compound to possess the latter and very little of the former, unlike what would be expected from the relative performance of meperidine and normeperidine, where relative addictiveness and antidepressant effectiveness are closely associated. Meperidine is more effective and also more addictive than normeperidine, whereas the compounds of the invention are as effective as meperidine, and relatively nonaddictive.

The compositions can be administered orally, parenterally or rectally in the form of, for example, tablets, capsules, suppositories, solutions or suspensions. One or a mixture of compounds can be administered together or in sequence. A series of doses of different compounds can be more effective than repeated doses of the same compound. The dose administered is sufficient to obtain an antidepressant effect, and can be from 50 to 800 mg. This can be by any mode of administration, such as by injection intra-muscularly or subcutaneously or by oral administration. A suitable daily dose in as many portions as desired is from 50 to 5000 mg.

The compound is suitably administered in dosage unit form. The term "dosage unit form" refers to single units each containing a dose of the active compound, generally in admixture with a pharmaceutical diluent therefor or otherwise in association with a pharmaceutical carrier. The amount of compound can be such that one or more units is required for a single dose. In the case of severable units, such as scored tablets, at least one fraction such as a half or quarter of a severable unit is required for single therapeutic administration. A dosage unit may contain, for example, from 50 to 800 mg. of compound or compounds.

A pharmaceutical carrier or diluent can be a solid, semi-solid or liquid material which serves as a vehicle, or medium for the active compound or compounds. Examples of diluents are water, alone or with varying proportions of ethanol, propylene glycol, polyethylene glycol 400, or similar solvents, and examples of solid carriers are lactose, dextrose, sucrose, sorbitol, mannitol, starch, gum acacia, calcium phosphate, liquid paraffin, cocoa butter, oil of theobroma, alginates, tragacanth, gelatine, syrup B.P., methyl cellulose, polyoxyethylene sorbitan monolaurate, and methyl- and propyl-hydroxyl-benzoate.

In the case of tablets, a lubricant may be incorporated to prevent sticking and binding of the powdered ingredients in the dies and on the punch of the tabletting machine. For such purpose, there may be employed for instance talc, aluminum, magnesium or calcium stearate or mineral oil.

The following are Examples of compositions for dosage units or other application forms in accordance with the invention:

Tablet formulation

| | Parts/tablet |
| --- | --- |
| Active compound | 15 |
| Lactose | 86 |
| Corn starch (dried) | 45.5 |
| Gelatin | 2.5 |
| Magnesium stearate | 1.0 |

The compound was powdered and passed through a sieve, and well mixed with the lactose and 30 mg. of the corn starch.

The mixed powders were combined with a warm gelatin solution prepared by stirring the gelatin in water and heating to form a 10% w./w. solution, granulated by passing through a B.S. No. 12 sieve, and the moist granules dried at 40° C.

The dried granules were re-granulated and the balance of the starch and the magnesium stearate were added and thoroughly mixed.

The granules were compressed to produce tablets each weighing 150 mg.

Tablet formulation

| | Parts/tablet |
| --- | --- |
| Active compound | 100 |
| Lactose | 39 |
| Corn starch (dried) | 80 |
| Gelatin | 4.0 |
| Magnesium stearate | 2.0 |

The method of preparation is identical with that of the preceding, except that 60 parts of starch is used in the granulation process and 20 parts during tableting.

Capsule formulation

| | Parts/capsule |
| --- | --- |
| Active compound | 250 |
| Lactose | 150 |

The compound and lactose were passed through a sieve and the powders well mixed together before filling into hard gelatin capsules of suitable size, so that each capsule contained 400 mg.

Suppositories

| | Parts/suppository |
| --- | --- |
| Active compound | 50 |
| Cocoa butter | 950 |

The compound was powdered and passed through a sieve and triturated with molten cocoa butter at 45° C. to form a smooth suspension.

The mixture was well stirred and poured into moulds, each of nominal 1 g. capacity, to produce suppositories.

Cachets

| | Parts/cachet |
| --- | --- |
| Active compound | 100 |
| Lactose | 400 |

The compound was passed through a sieve, mixed with lactose previously sieved and filled into cachets of suitable size so that each contained 500 mg.

Intramuscular injection (suspension in aqueous vehicle)

| | Parts |
| --- | --- |
| Compound | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml. | |

The sodium citrate and sodium carboxymethylcellulose were mixed with sufficient water for injection at 80° C. The mixture was cooled to 50° C. and the methyl and propyl para-hydroxybenzoates added followed by the medicament previously milled and sieved 300 mesh. When cooled the injection was made up to volume and sterilized by heating in an autoclave.

Having regard to the foregoing disclosure, the following is claimed as the inventive and patentable embodiment thereof:

1. A method of treating an animal having depression which comprises administering to the animal an amount effective to ameliorate depression of a compound selected from the group consisting of a compound having the formula:

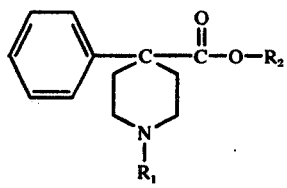

in which $R_1$ is selected from the group consisting of lower alkyl having from one to four carbon atoms and allyl and $R_2$ is alkyl having from one to two carbon atoms; but if $R_1$ is methyl or ethyl, $R_2$ is other than ethyl; and the compound in the form of a pharmaceutically acceptable salt thereof.

2. A method according to claim 1, wherein $R_1$ and $R_2$ are each methyl.

3. A method according to claim 1, wherein $R_1$ is n-propyl and $R_2$ is ethyl.

4. A method according to claim 1, wherein $R_1$ is n-butyl and $R_2$ is ethyl.

5. A method according to claim 1, wherein $R_1$ is allyl and $R_2$ is ethyl.

6. A method according to claim 1, in which the compound administered is in dosage unit form.

7. A method according to claim 1, in which the amount of compound administered per dose is within the range of from about 50 to about 800 mg.

8. A pharmaceutical composition in dosage unit form for use in treating an animal having depression comprising from about 50 to about 800 mg. of a compound selected from the group consisting of a compound having the formula:

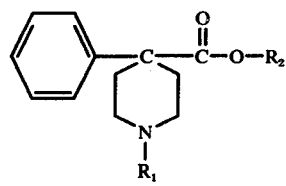

in which $R_1$ is selected from the group consisting of lower alkyl having from one to four carbon atoms and allyl and $R_2$ is alkyl having from one to two carbon atoms; but if $R_1$ is methyl or ethyl, $R_2$ is other than ethyl; and the compound in the form of a pharmaceutically acceptable salt thereof, in association with a pharmaceutically acceptable carrier.

9. A composition according to claim 8, comprising a diluent and in liquid form.

10. A composition according to claim 8, comprising a solid carrier and in solid form.

* * * * *

UNITED STATES PATENT OFFICE
CERTIFICATE OF CORRECTION

Patent No. 4,021,565　　　　　　　　　Dated May 3, 1977

Inventor(s) Frank M. Berger

It is certified that error appears in the above-identified patent and that said Letters Patent are hereby corrected as shown below:

| | | |
|---|---|---|
| Column 1, lines 18-19 | : | "consumated" should be --consummated-- |
| line 24 | : | "casual" should be --causal-- |
| line 51 | : | add -- a -- before "prerequisite" |
| Column 2, line 20 | : | "merperidine" should be --meperidine-- |
| line 59 | : | "alkyl" should be --allyl-- |
| line 63 | : | "alkyl" should be --allyl-- |
| Column 3, line 41 | : | "1945" should be -- 1945 -- |
| line 49 | : | "1944" should be -- 1944 -- |
| line 57 | : | "1947" should be -- 1947 -- |
| Column 5, line 68 | : | "less" should be -- leap -- |

Signed and Sealed this

Twenty-seventh Day of September 19

[SEAL]

Attest:

RUTH C. MASON　　　　　　　LUTRELLE F. PARKER
Attesting Officer　　　　Acting Commissioner of Patents and Tradema